United States Patent
Mooradian et al.

(10) Patent No.: US 8,932,364 B2
(45) Date of Patent: Jan. 13, 2015

(54) PROSTHETIC KNEE VOID FILERS WITH SPLINED FIXATION

(75) Inventors: Mark Mooradian, Phoenix, AZ (US); Jeffery Arnett, Gilbert, AZ (US); Joshua A. Butters, Chandler, AZ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 430 days.

(21) Appl. No.: 13/182,841

(22) Filed: Jul. 14, 2011

(65) Prior Publication Data

US 2012/0016482 A1 Jan. 19, 2012

Related U.S. Application Data

(60) Provisional application No. 61/364,070, filed on Jul. 14, 2010.

(51) Int. Cl.
| | | |
|---|---|---|
| *A61F 2/42* | (2006.01) | |
| *A61F 2/30* | (2006.01) | |
| *A61F 2/38* | (2006.01) | |

(52) U.S. Cl.
CPC ........... *A61F 2/30734* (2013.01); *A61F 2/3886* (2013.01); *A61F 2/389* (2013.01); *A61F 2002/30354* (2013.01); *A61F 2002/30405* (2013.01); *A61F 2002/3054* (2013.01); *A61F 2002/30884* (2013.01)
USPC ............... 623/20.32; 623/20.33; 623/20.34; 623/20.35

(58) Field of Classification Search
CPC ...... A61F 2/389; A61F 2/3859; A61F 2/3886
USPC .......... 623/18.11, 20.15, 22.42, 20.32, 20.33, 623/20.34
See application file for complete search history.

(56) References Cited

U.S. PATENT DOCUMENTS

| | | | | |
|---|---|---|---|---|
| 4,634,444 | A | | 1/1987 | Noiles |
| 4,790,852 | A | | 12/1988 | Noiles |
| 4,822,366 | A | | 4/1989 | Bolesky |
| 4,938,769 | A | * | 7/1990 | Shaw .......................... 623/20.15 |
| 5,011,496 | A | | 4/1991 | Forte et al. |
| 5,152,797 | A | * | 10/1992 | Luckman et al. .......... 623/20.16 |
| 5,282,866 | A | * | 2/1994 | Cohen et al. ............... 623/20.34 |
| 5,290,313 | A | | 3/1994 | Heldreth |
| 5,480,445 | A | * | 1/1996 | Burkinshaw ............... 623/20.32 |
| 5,489,311 | A | | 2/1996 | Cipolletti |

(Continued)

FOREIGN PATENT DOCUMENTS

WO 2008118247 A1 10/2008

*Primary Examiner* — Thomas J Sweet
*Assistant Examiner* — Seema Mathew
(74) *Attorney, Agent, or Firm* — Lerner, David, Littenberg, Krumholz & Mentlik, LLP

(57) ABSTRACT

Disclosed herein are systems and methods for filling bone voids which may be present at the time of surgery. The systems disclosed herein generally include a baseplate component, a spacer component, and void filler component. The spacer component is generally assembled to the baseplate component with a taper or press-fit, for example, in one of a plurality of selected axial positions. The void filler component is then generally assembled to the spacer component in one of a plurality of selected axial positions. The void filler component preferably has an outer surface with portions having varying diameters such that the outer surface thereof can be received within a canal of a bone and contact the bone forming the canal at different locations in order to aid in stabilizing the assembled components in the canal.

24 Claims, 10 Drawing Sheets

(56) References Cited

U.S. PATENT DOCUMENTS

| | | | |
|---|---|---|---|
| 5,613,970 A | 3/1997 | Houston et al. | |
| 5,702,461 A * | 12/1997 | Pappas et al. | 623/20.34 |
| 5,782,920 A * | 7/1998 | Colleran | 623/20.34 |
| 5,782,921 A | 7/1998 | Colleran et al. | |
| 5,824,097 A | 10/1998 | Gabriel et al. | |
| 6,039,764 A | 3/2000 | Pottenger et al. | |
| 6,071,311 A | 6/2000 | O'Neil et al. | |
| 6,146,424 A | 11/2000 | Gray, Jr. et al. | |
| 6,162,255 A | 12/2000 | Oyola | |
| 6,171,342 B1 | 1/2001 | O'Neil et al. | |
| 6,214,052 B1 | 4/2001 | Burkinshaw | |
| 6,527,807 B1 | 3/2003 | O'Neil et al. | |
| 6,942,670 B2 * | 9/2005 | Heldreth et al. | 606/102 |
| 7,025,788 B2 * | 4/2006 | Metzger et al. | 623/20.15 |
| 7,182,786 B2 * | 2/2007 | Justin et al. | 623/20.15 |
| 7,291,174 B2 | 11/2007 | German et al. | |
| 7,497,874 B1 | 3/2009 | Metzger et al. | |
| 7,691,150 B2 | 4/2010 | Cronin et al. | |
| 7,753,960 B2 * | 7/2010 | Cipolletti et al. | 623/20.29 |
| 7,771,484 B2 * | 8/2010 | Campbell | 623/20.34 |
| 7,799,085 B2 | 9/2010 | Goodfried et al. | |
| 7,806,936 B2 | 10/2010 | Wright | |
| 7,842,093 B2 * | 11/2010 | Peters et al. | 623/20.15 |
| 7,892,288 B2 | 2/2011 | Blaylock et al. | |
| 8,540,775 B2 * | 9/2013 | Reich et al. | 623/20.15 |
| 2003/0055509 A1 * | 3/2003 | McCue et al. | 623/20.32 |
| 2004/0030397 A1 * | 2/2004 | Collazo | 623/20.32 |
| 2004/0049285 A1 | 3/2004 | Haas | |
| 2004/0049286 A1 * | 3/2004 | German et al. | 623/20.33 |
| 2004/0162619 A1 * | 8/2004 | Blaylock et al. | 623/20.16 |
| 2004/0220677 A1 * | 11/2004 | Delfosse et al. | 623/20.33 |
| 2005/0004679 A1 * | 1/2005 | Sederholm et al. | 623/22.42 |
| 2005/0107883 A1 | 5/2005 | Goodfried et al. | |
| 2005/0222686 A1 * | 10/2005 | Brehm | 623/20.33 |
| 2006/0030945 A1 * | 2/2006 | Wright | 623/20.15 |
| 2006/0167554 A1 * | 7/2006 | Heck et al. | 623/20.15 |
| 2007/0100463 A1 * | 5/2007 | Aram et al. | 623/20.29 |
| 2007/0162145 A1 * | 7/2007 | Justin et al. | 623/20.32 |
| 2007/0179628 A1 * | 8/2007 | Rochetin | 623/20.34 |
| 2008/0021566 A1 | 1/2008 | Peters et al. | |
| 2008/0051908 A1 * | 2/2008 | Angibaud et al. | 623/20.32 |
| 2008/0091271 A1 * | 4/2008 | Bonitati et al. | 623/20.34 |
| 2008/0097614 A1 | 4/2008 | Wright | |
| 2008/0114464 A1 * | 5/2008 | Barnett et al. | 623/20.33 |
| 2008/0119941 A1 * | 5/2008 | Seo et al. | 623/20.34 |
| 2010/0057212 A1 * | 3/2010 | Thomas | 623/20.32 |
| 2010/0076565 A1 | 3/2010 | Thomas | |
| 2010/0114323 A1 | 5/2010 | Deruntz et al. | |
| 2010/0222890 A1 * | 9/2010 | Barnett et al. | 623/20.33 |
| 2011/0009974 A1 | 1/2011 | Blaylock et al. | |
| 2011/0066249 A1 * | 3/2011 | Justin et al. | 623/20.32 |
| 2012/0059484 A1 * | 3/2012 | Justin et al. | 623/20.34 |
| 2012/0310361 A1 * | 12/2012 | Zubok et al. | 623/20.32 |
| 2012/0323333 A1 * | 12/2012 | Metzger | 623/20.32 |
| 2013/0006370 A1 * | 1/2013 | Wogoman et al. | 623/20.16 |
| 2013/0006376 A1 * | 1/2013 | Wogoman et al. | 623/20.32 |
| 2013/0006377 A1 * | 1/2013 | Waite et al. | 623/20.32 |
| 2013/0325136 A1 * | 12/2013 | Thomas et al. | 623/20.32 |
| 2014/0081411 A1 * | 3/2014 | Lieberman et al. | 623/20.15 |

* cited by examiner

PROSTHETIC KNEE VOID FILLERS WITH SPLINED FIXATION

CROSS-REFERENCE TO RELATED APPLICATION

This application claims the benefit of the filing date of U.S. Provisional Patent Application No. 61/364,070 filed Jul. 14, 2010, the disclosure of which is hereby incorporated herein by reference.

FIELD OF THE INVENTION

The present invention relates to joint prosthesis systems for filling voids in bones of a patient, and in particular it relates to assembling together the components of a joint prosthesis system in order fill a void in bone as needed and to properly position a support surface of the joint prosthesis system for receiving a corresponding prosthesis.

BACKGROUND OF THE INVENTION

Joint replacement surgery is a common orthopedic procedure for joint such as the shoulder, hip, knee, ankle and wrist. Prior to implanting prosthetic components in a joint of a patient, a surgeon generally has to resect at least a portion of the patient's native bone in order to create a recess or cavity for receiving at least a portion of the prosthetic components being implanted. During the process of resecting bone, a surgeon generally only resects the amount of bone that is needed in order to implant the prosthetic components in the joint replacement surgery properly. Once bone is resected from a joint, it generally can no longer be replaced with native bone. Thus, the surgeon attempts to maintain as much native structural integrity of the joint as he or she can during the resection process.

An issue generally encountered by surgeons replacing joints is the loss of native bone near the joint being replaced. Defects in a bone adjacent a joint, such as the hip or knee, can occur due to wear and arthritis of the joint, congenital deformity, and following the removal of a failed prosthetic component. When prosthetic components fail for any one of a variety of reasons, a revision procedure is often necessary. When the failed prosthetic component or components are removed from the joint during a revision procedure, it is common for there to have been further native bone loss in the area adjacent the originally implant position of the prosthetic component or components due to movement of the component or components after implantation or even degeneration or further degeneration of the bone.

The use of bone graft or cement is known to position prosthetic components with respect to bone or to fill voids in bone. Bone graft and cement is also known to stabilize the position and location of prosthetic components in bone. While bone graft or cement is widely used in orthopedic surgery, in cases where there is a large void in bone it is preferable to implant a solid structure in bone for proper support of a prosthetic component in the bone. It is also known to attach augments and stems to prosthetic components in order to aid in the stabilization of prosthetic components in bone. While such augments and stems are used, the available augments and stems that can be attached to prosthetic components generally do not fill the void sufficiently to stabilize the prosthetic components effectively in bone.

There is a need for a joint prosthesis system that optimizes contact with native bone and with minimal removal of native bone and that encourages bone ingrowth and attachment over as large a surface area as possible. There is also a need for giving surgeons the opportunity to attach void fillers to prosthetic components in a plurality of different positions and orientations in order to fill voids sufficiently to stabilize the prosthetic components effectively in bone.

BRIEF SUMMARY OF THE INVENTION

A first aspect of the present invention is a joint prosthesis system comprising a baseplate component, a spacer component, and a void filler component. The baseplate component preferably has a top surface and a bottom surface, the bottom surface having a stem portion protruding outwardly therefrom, the stem portion having at least one rib located along at least a portion of a length thereof. The spacer component preferably has a top surface, a bottom surface, an inner surface, an outer surface, and an aperture extending through the top and bottom surfaces thereof, the inner surface having at least one recess formed therein and the outer surface having at least one protrusion extending outwardly therefrom. The void filler component preferably has a top surface, a bottom surface, an inner surface, an outer surface, and an aperture extending through the top and bottom surfaces thereof, the inner surface having at least one recess formed therein.

In one embodiment of this first aspect of the present invention, the spacer component is preferably coupled to the baseplate component when the aperture of the spacer component receives the stem portion of the baseplate component and the at least one rib of the stem portion is located in the at least one recess of the spacer component. The void filler component is preferably coupled to the spacer component when the aperture of the void filler component receives the outer surface of the spacer component and the at least one protrusion of the spacer component is located in the at least one recess of the void filler component.

In one embodiment of this first aspect of the present invention, the baseplate component is a tibial component. Preferably, the upper surface of the baseplate component is a flat surface adapted to receive a tibial insert having an upper surface adapted for engaging an articulating implant.

In another embodiment, the baseplate component is a femoral component.

In yet another embodiment of this first aspect of the present invention, the stem portion of the baseplate has a tapered outer surface. Preferably, a bottom surface of the stem portion is adapted to receive stem adapter therein. The stem adapter may be coupled to the stem portion by a locknut. In one embodiment, a second stem portion may be coupled to the stem adapted in order to lengthen the joint prosthesis system.

In still yet another embodiment, first and second ribs preferably extend outwardly from the stem portion of the baseplate component, wherein each rib extends along at least a portion of a length of the outer surface of the stem portion and are located at different locations around a circumference thereof.

In still yet another embodiment of this first aspect of the present invention, first and second keels preferably extend outwardly from the stem portion of the baseplate component, wherein each rib extends along at least a portion of a length of the outer surface of the stem portion and are located at different locations around a circumference thereof.

In still yet another embodiment, the spacer component includes an aperture extending through the outer and inner surfaces thereof forming a first space and a second space located around a circumference of the spacer component such that a portion of the first keel can be received in the first space and a portion of the second keel can be received in the second space when the spacer component is coupled to the stem portion of the baseplate component.

In another embodiment, the inner surface of the spacer component may include two or three recesses therein. In other embodiment, the inner surface of the spacer component may include more than three recesses therein. Preferably, the recesses are located approximately 30° apart from one another in the inner surface of the spacer component. In one embodiment, the recesses may be located approximately 5° apart and in other embodiments may be located approximately 85° degrees apart or may be located any number of degrees between 5° and 85° degrees apart.

In one embodiment, the void filler component includes a plurality of sections having differing diameters. The diameters of the plurality of sections preferably decrease from the top surface to the bottom surface of the void filler component.

In another embodiment, the inner surface of the void filler component may include two or three recesses therein. In other embodiment, the inner surface of the void filler component may include more than three recesses therein. Preferably, the recesses are located approximately 30° apart from one another in the inner surface of the void filler component. In one embodiment, the recesses may be located approximately 5° apart and in other embodiments may be located approximately 85° degrees apart or may be located any number of degrees between 5° and 85° degrees apart.

In one embodiment of this first aspect of the present invention, the stem portion of the baseplate component has a longitudinal axis and the aperture of the spacer component has a longitudinal axis and when the spacer component is coupled to the stem portion of the baseplate component the longitudinal axes thereof are coaxial.

In another embodiment, the stem portion of the baseplate component has a longitudinal axis and the aperture of the spacer component has a longitudinal axis and when the spacer component is coupled to the stem portion of the baseplate component the longitudinal axes thereof are parallel and offset from one another.

In one embodiment, the aperture of the void filler component has a longitudinal axis and when the void filler component is coupled to the spacer component the longitudinal axes thereof are coaxial.

In another embodiment, the aperture of the void filler component has a longitudinal axis and when the void filler component is coupled to the spacer component the longitudinal axes thereof are parallel and offset from one another.

In one embodiment, the aperture of the void filler component has a longitudinal axis and when the void filler component is coupled to the spacer component the longitudinal axes thereof are coaxial.

In another embodiment, the aperture of the void filler component has a longitudinal axis and when the void filler component is coupled to the spacer component the longitudinal axes thereof are parallel and offset from one another.

A second aspect of the present invention is a method of stabilizing a joint prosthesis system including a baseplate component, a spacer component, and a void filler component in a canal of a bone. The method preferably includes assembling at least one of a plurality of recesses of the spacer component to at least one of a plurality of ribs of a stem portion protruding outwardly from a bottom surface of the baseplate component and assembling at least one of a plurality of recesses of the void filler component to at least one of a plurality of protrusions of the spacer component. The method preferably further includes implanting the assembled baseplate, spacer and void filler components into the canal of the bone.

In one embodiment of this second aspect of the present invention, the plurality of recesses are located about a circumference of an inner surface of the spacer component. Preferably, the plurality of ribs are located along at least a portion of a length of the stem portion of the baseplate component. Preferably, the plurality of protrusions are located along at least a portion of a length of an outer surface of the spacer component.

In another embodiment of this second aspect of the present invention, the assembled baseplate, spacer and void filler components are implanted into the canal of the bone such that at least a portion of an outside surface of the void filler component contacts the bone forming the canal.

In another embodiment, the void filler may be implanted into a bone canal and be positioned within the canal and a spacer component assembled to a baseplate component may then be received within the aperture of the void filler component at a desired location.

In yet another embodiment, the engagement of the spacer component to the baseplate component prohibits axial rotation of the spacer and baseplate components with respect to one another. Preferably, the axial rotation is prohibited along a longitudinal axis of the joint prosthesis system.

In yet another embodiment, engagement of the void filler component to the spacer component prohibits axial rotation of the void filler and spacer components with respect to one another. Preferably, the axial rotation is prohibited along a longitudinal axis of the joint prosthesis system.

In another aspect of the present invention a void filler may be oriented at one of multiple possible angles with respect to a tibial prosthesis during implantation of the components into a bone canal. This capability for multiple implant angles is preferable because tibial voids can occur at a range of orientations and this capability allows the void filler to be implanted with minimal removal of native bone.

In one embodiment, the void filler may be oriented with respect to the tibial prosthesis at one of multiple possible angles using a spline-and-slot arrangement. The advantage of this design is that, in comparison to fixing the rotation by impacting a Morse taper feature, this method is less sensitive to user technique and strength of force application.

In another embodiment, fine angular adjustments, such as 3 degrees, may be made between the rotational orientation of the void filler and tibial prosthesis. The combination of fine adjustments and robust components is achieved by having multiple attachment orientations for each of the baseplate, spacer, and void filler components.

In another embodiment, revisions to the angular orientation of the spacer component and the baseplate component with respect to the void filler component can be made without the need to remove the void filler component from its implanted position within a bone canal in bone.

One embodiment of the present invention is the splined attachment method, which permits rotational fixation of the void filler at multiple orientations without requiring the impaction of a tapered joint.

Another embodiment of the present invention is the use of two splined attachment joints, with a relatively small difference in angular spacing of the two attachment joints, so that splined features can be large (and thus mechanically strong) yet still provide for fine rotational adjustment.

Another embodiment of the present invention is the use of a splined spacer component between a baseplate component and a void filler component, in which the splined spacer component is available in multiple versions with different relative rotation between internal and external fixation features, so that changing spacer components can provide a different range of relative angles between the void filler component and baseplate component.

Another embodiment of the present invention is the use of a spacer component between a baseplate component and a void filler component, in which the spacer component has internal and external fixation features which are relatively either concentric or eccentric, so that changing spacer components can provide a desired positional offset between the void filler component and the baseplate component.

Another embodiment of the present invention uses the combination of baseplate component, spacer component, void filler component, and an offset stem adapter. A stem portion of the offset stem adapter preferably has an axis that does not need to coincide with an axis of the assembled baseplate, spacer and void filler components. This feature allows better anatomic fits for both the void filler component and the stem portion, and minimizes the need to remove sound bone.

Another embodiment of the present invention is the combination of a baseplate component, a spacer component, a void filler component, and an offset stem adapter. In this embodiment, the baseplate component, the spacer component, and the offset stem adapter may be removed while leaving the void filler component implanted. The ability to remove (revise) components separately preferably makes the revision process easier for the surgeon.

DESCRIPTION OF THE FIGURES

A more complete appreciation of the subject matter of the present invention and the various advantages thereof can be realized by reference to the following detailed description in which reference is made to the accompanying drawings in which.

DETAILED DESCRIPTION

As used herein, when referring to the drill guides of the present invention, the term "proximal" means closer to the surgeon or in a direction toward the surgeon and the term "distal" means more distant from the surgeon or in a direction away from the surgeon. The term "anterior" means towards the front part of the body or the face and the term "posterior" means towards the back of the body. The term "medial" means toward the midline of the body and the term "lateral" means away from the midline of the body.

Figure 1:
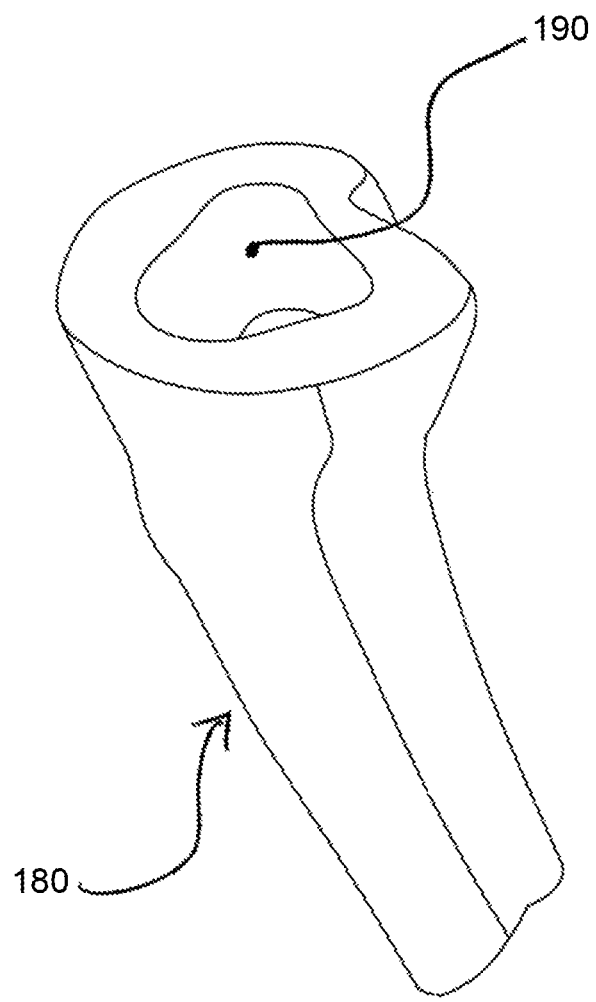
FIG. 1 is an isometric view of an exemplary bone having a canal therein.
Figure 2:
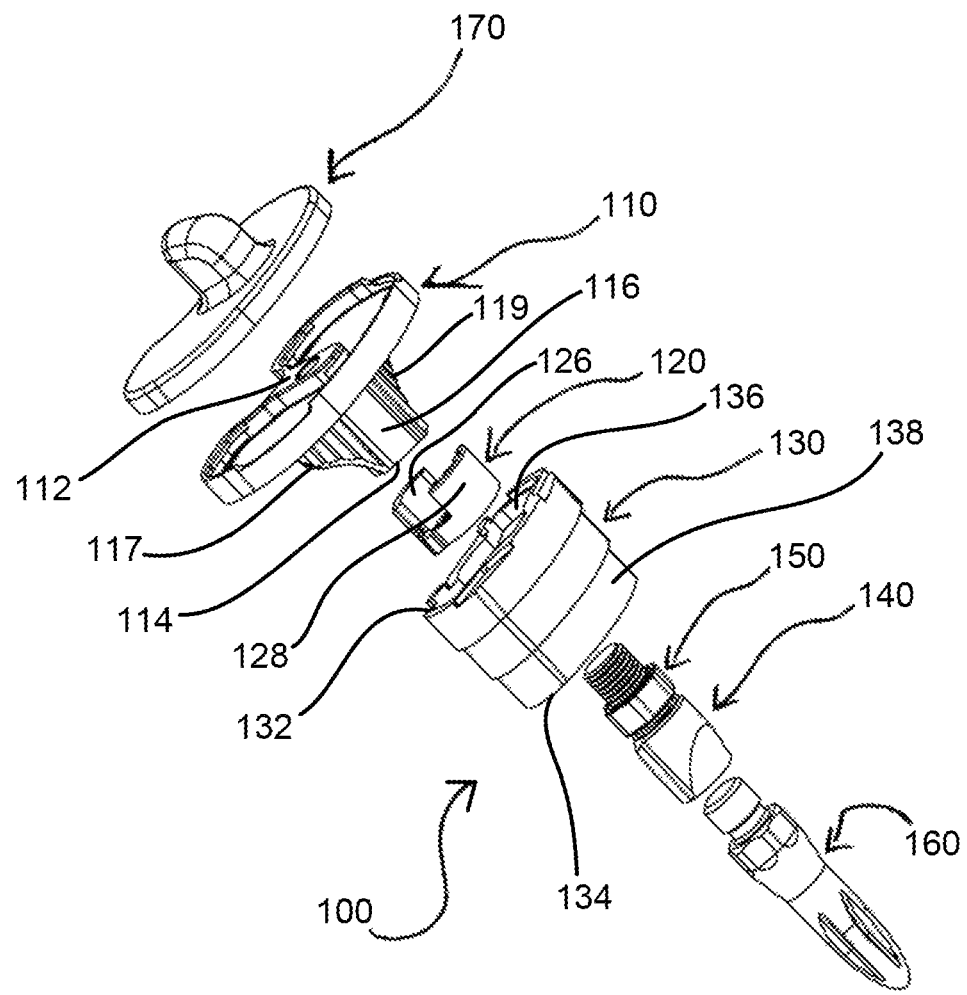
FIG. 2 is an exploded isometric view of one embodiment of a joint prosthesis system of the present invention.
Figure 3:
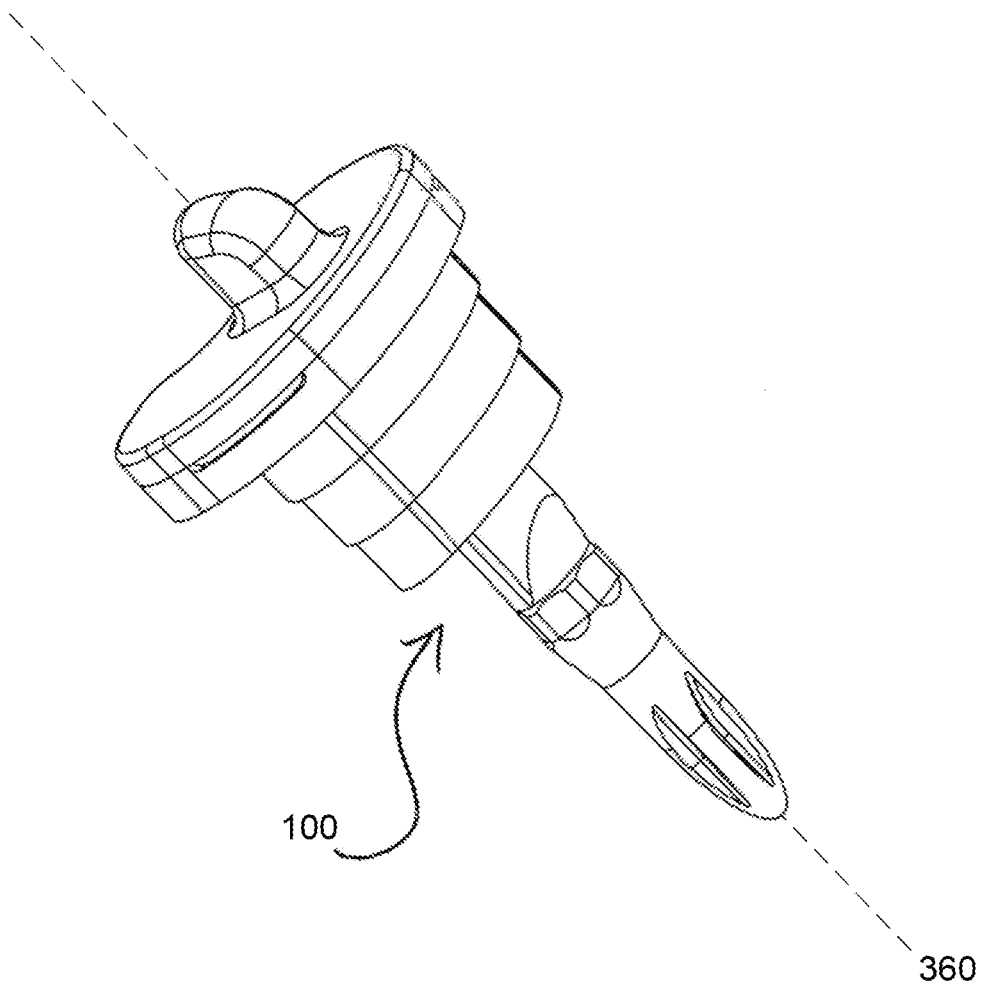
FIG. 3 is an assembled isometric view of the joint prosthesis system shown in FIG. 2.

FIG. 1 shows a bone 180 having a canal 190. Bone 180 may be any type of bone, but as shown it represents a tibia of a patient. Canal 190 can be formed through a reaming procedure or may be present due to a previous joint replacement procedure in which a tibial prosthesis was implanted in canal 190 and has now been removed leaving a void in bone 180. Canal 190 can also be present because of bone degeneration such as osteoporosis. The present invention includes systems and methods for implanting a joint prosthesis in order fill a void in bone as needed, such as canal 190, and to properly position a support surface of the joint prosthesis for receiving a corresponding prosthesis such as a tibial or femoral insert.

Referring to FIGS. 2-14, there is shown an embodiment of a joint prosthesis system of the present invention designated generally by reference numeral 100. As shown in those figures, system 100 includes a baseplate component 110, a spacer component 120, a void filler component 130, an adapter component 140, a locknut, a stem component 160 and an insert component 170.

Baseplate component 110 preferably has a top surface 112 and a bottom surface 114, the bottom surface having a stem portion 116 protruding outwardly therefrom, the stem portion having at least one rib 210 located along at least a portion of a length thereof. First and second keels 117, 119 preferably extend outwardly from the stem portion 116 of the baseplate component 110, wherein each rib 210 extends along at least a portion of a length of the outer surface of the stem portion and are located at different locations around a circumference thereof.

Spacer component 120 preferably has a top surface 122, a bottom surface 124, an inner surface 126, an outer surface 128, and an aperture 129 extending through the top and bottom surfaces 124, 122 thereof. Inner surface 126 preferably has at least one recess 200 formed therein and the outer surface 128 preferably has at least one spline or protrusion 220 extending outwardly therefrom. Spacer component 120 preferably includes an aperture 125 extending through the inner and outer surfaces 126, 128 thereof forming a first space 127a and a second space 127b located around a circumference of the spacer component such that a portion of the first keel 117 can be received in the first space 127a and a portion of the second keel 119 can be received in the second space 127b when the spacer component 120 is coupled to the stem portion 116 of the baseplate component 110.

Void filler component 130 preferably has a top surface 132, a bottom surface 134, an inner surface 136, an outer surface 138, and an aperture 139 extending through the top and bottom surfaces 132, 134 thereof, the inner surface 136 having a plurality of recesses 230, 240, 250 formed therein. Outer surface 138 of void filler component preferably includes a plurality of sections having different diameters. Preferably, the diameters of the sections decrease form the top surface 132 to the bottom surface 134. Examples of properties of void filler component 130 is aiding in carrying patient weight by distributing the weight over the remaining bone, such as bone 180; and providing stability by helping to position the baseplate component 110 and preventing undesired rotation thereof.

Spacer component 120 is coupled to baseplate component 110 when aperture 129 of the spacer component 120 receives the stem portion 116 of the baseplate component 110 and the at least one rib 210 of the stem portion 116 is located in the at least one recess 200 of the spacer component 120.

Void filler component 130 is coupled to the spacer component 120 when the aperture 139 of the void filler component 130 receives the outer surface 128 of the spacer component 120 and the at least one protrusion 220 of the spacer component 120 is located in the at least one recess 230, 240, 250 of the void filler component 130. Void filler component 130 preferably slides over spacer component 120 and provides support for the baseplate component 110 in joint prosthesis system 100.

Adapter component 140 preferably fastens to stem portion 116 of baseplate component 110 with locknut 150. Stem component 160 preferably fastens into adapter component 140. Insert component 170 preferably rests on top surface 112 of baseplate component 110. In an alternative embodiment, stem component 160 could connect directly to stem portion 116.

Spacer component 120 preferably includes a longitudinal axis 320 passing through the center of spacer component 120 in a superior to inferior direction or vice versa. Alternatively, spacer component may be offset such that longitudinal axis 320 does not pass through the center of spacer component 120. Void filler component 130 preferably includes a longitudinal axis 360 passing through the center of void filler component 130 in a superior to inferior direction or vice versa. Alternatively, void filler component 130 may be offset such that longitudinal axis 360 does not pass through the center of void filler component 130.

Figure 4:
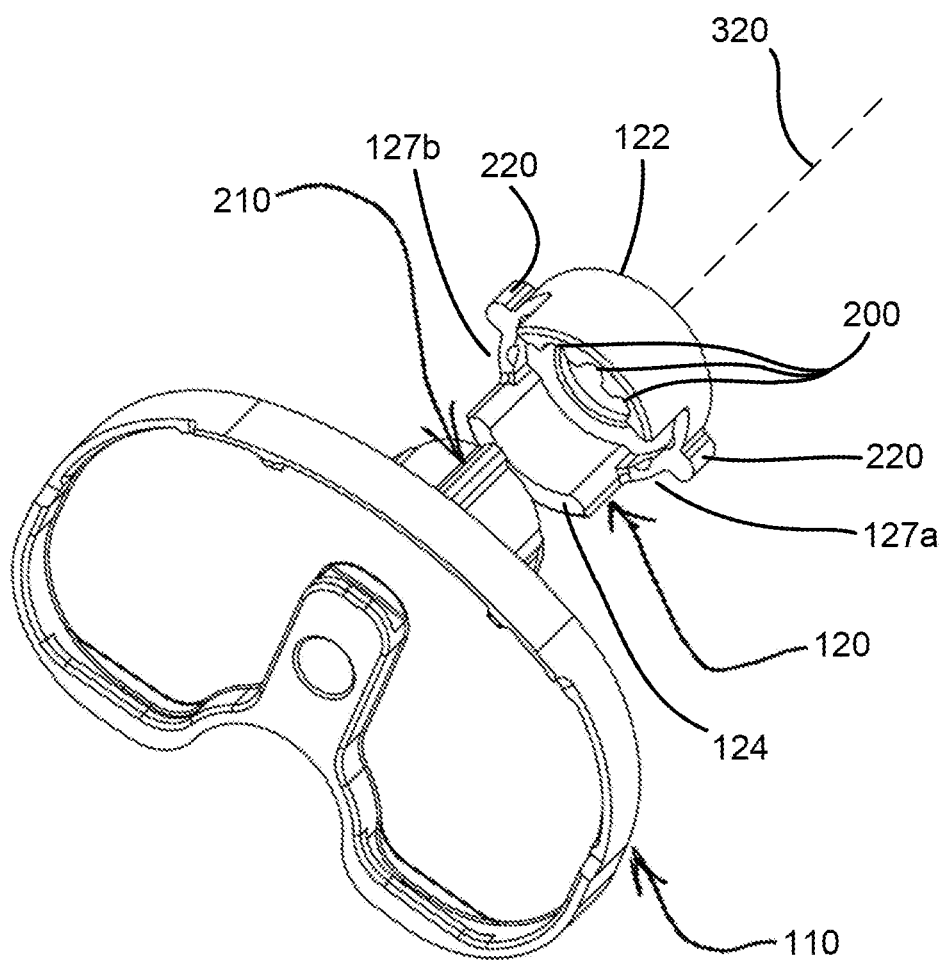
FIG. 4 is a top isometric view of one embodiment of a baseplate component and a spacer component of the present invention showing a rib of the baseplate component aligned for engagement with a recess of the spacer component.

As shown in FIG. 4, the spacer component 120 includes three orientation slots or recesses 200 to define its angular orientation as it is installed on the baseplate component 110. These three slots 200 are angularly spaced approximately 30 degrees apart from the longitudinal axis 320 of the spacer component 120. During assembly, one of these orientation slots or recesses 200 is mated with a indexing boss or rib 121 on the baseplate component 110. While this embodiment shows three orientation slots, which are spaced approximately 30 degrees apart, other embodiments may contain a different number of slots and may be spaced different degrees apart.

Figure 5:
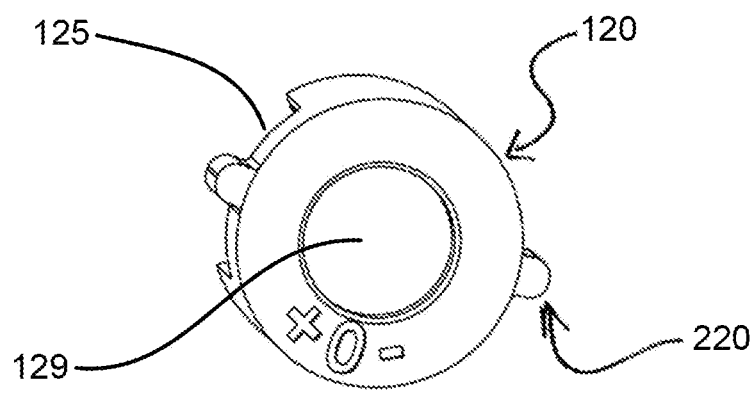
FIG. 5 is a bottom isometric view of the spacer component shown in FIG. 4.
Figure 6:
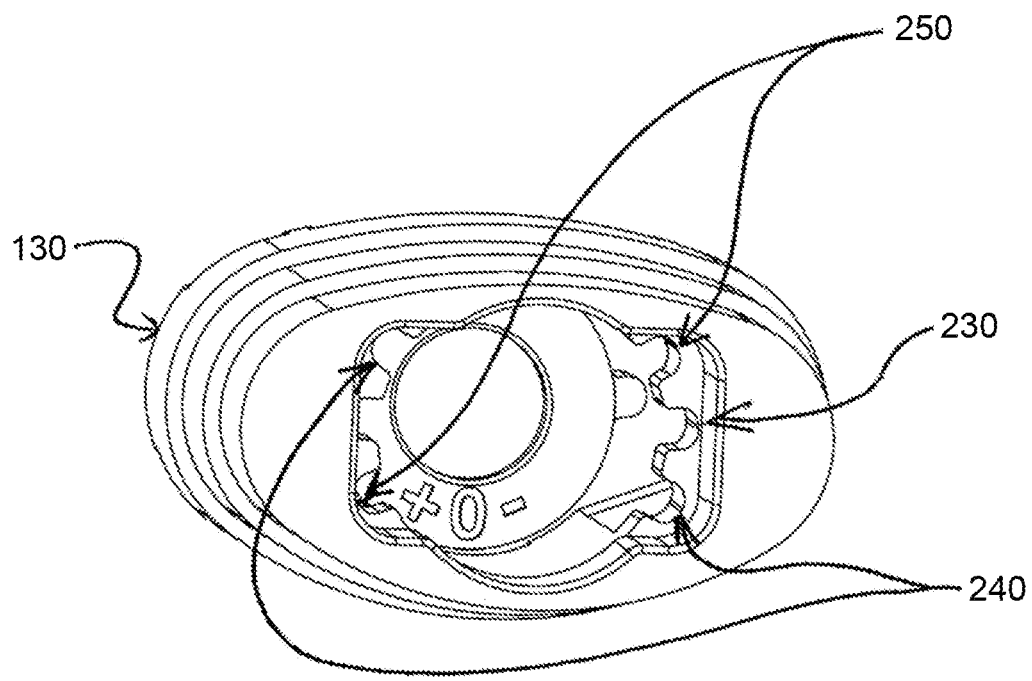
FIG. 6 is a bottom isometric view showing the spacer component of FIG. 5 in a position just prior to being assembled to a void filler component.

As shown in FIG. 5, the spacer component 120 includes external spline features or protrusions 220. As shown in FIG. 6, these features mate with corresponding slots or recess pairs 230, 240, 250 in the void filler component 130. The recess pairs 230, 240, 250 provide different installation angles between the spacer component 120 and the void filler component 130. Slot pairs 240 and 250 are preferably oriented 27 degrees clockwise and counterclockwise, respectively, from the central pair of slots 230. Slot pairs 240 and 250 may be oriented between 5 and 85 degrees clockwise and counterclockwise, respectively, from central pair of slots 230. While this embodiment shows three recess pairs spaced apart approximately 27 degrees, other embodiments may contain a different number of recess pairs and may be spaced different degrees apart.

Figure 7:
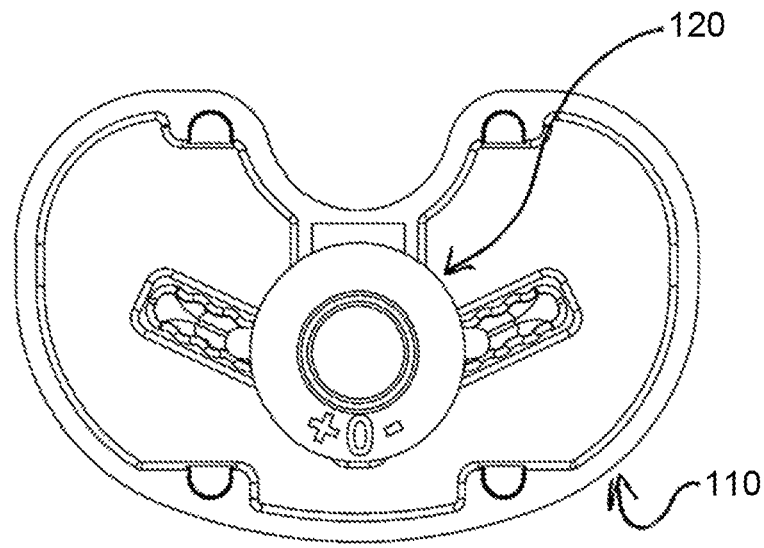
FIG. 7 is a bottom view of one embodiment of a spacer component assembled to a baseplate component.
Figure 8:
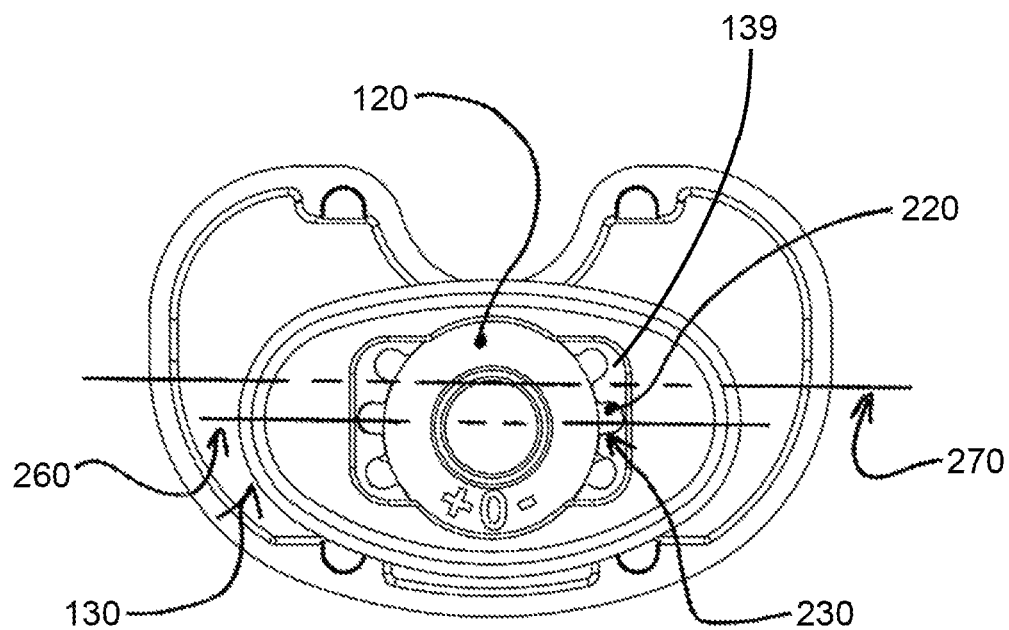
FIG. 8 is a bottom view of the assembled spacer and baseplate components shown in FIG. 7 including a void filler component assembled to the assembled spacer and baseplate components with a horizontal axis of the void filler component being parallel to a horizontal axis of the baseplate component.

FIG. 7 shows a bottom view of the baseplate component 110 with the spacer component 120 installed with the central slot of the three orientation slots 200 (not shown) mated with the indexing boss or rib 210 (not shown) of the baseplate component 110. FIG. 8 shows the void filler component 130 installed with its central slots 230 mating with the external spline features 220 of the spacer component 120. As can be seen in FIG. 8, a horizontal axis 260 of the void filler component 130 is aligned parallel with a horizontal axis 270 of the baseplate component 110.

Figure 9:
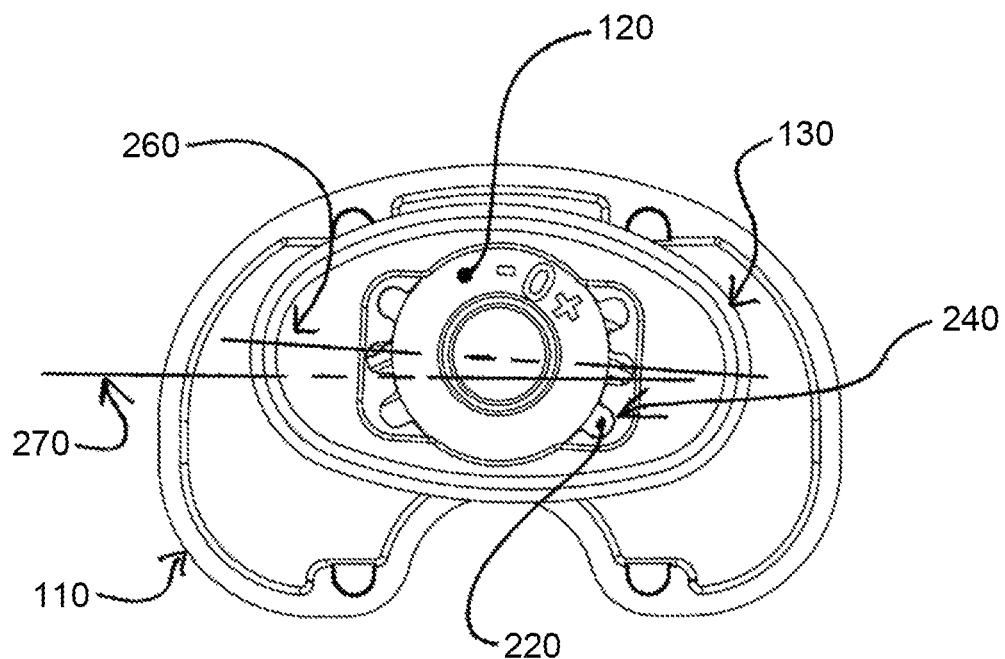
FIG. 9 is a bottom assembled view of the baseplate, spacer, and void filler components shown in FIG. 8 with a horizontal axis of the void filler component being angled with respect to the horizontal axis of the baseplate component.

FIG. 9 shows the baseplate component 110 installed or assembled with the spacer component 120 with the left-most slot of its three orientation slots 200 (not shown) mated with the indexing boss or rib 210 (not shown) of the baseplate component 110. This view also shows the void filler component 130 installed with alternate slots 240 mating with the external spline features 220 of the spacer component 120. In this assembly orientation, the horizontal axis 260 of the void filler component 130 preferably makes a 3 degree clockwise angle to the horizontal axis 270 of the baseplate component 110 (3 degrees being the difference between the 30 degree angular spacing on the spacer component 120 and the 27 degree spacing on the void filler component 130.

Figure 10:
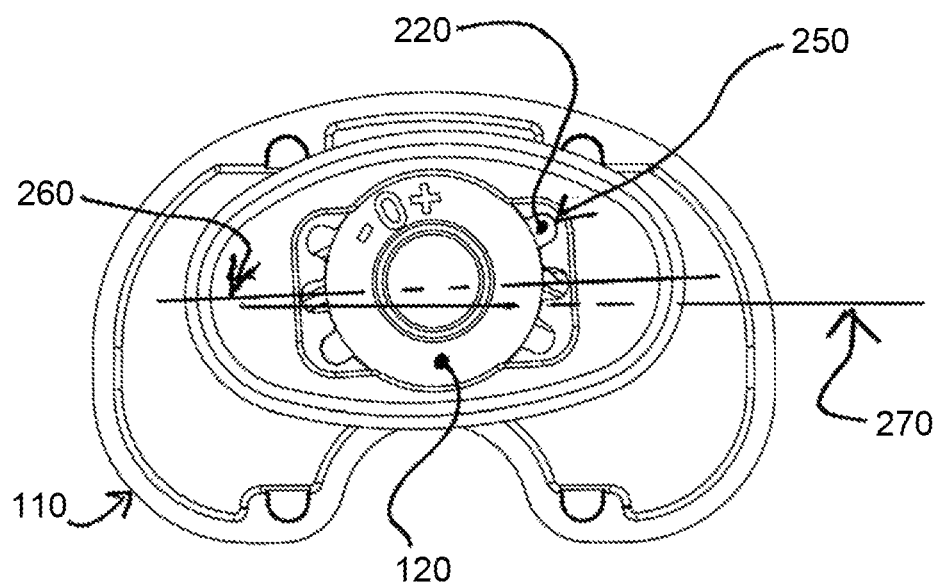
FIG. 10 is a bottom assembled view of the baseplate, spacer, and void filler components shown in FIG. 9 with a horizontal axis of the void filler component being angled with respect to the horizontal axis of the baseplate component in an alternate configuration as shown in FIG. 9.

FIG. 10 shows the baseplate component 110 installed with the spacer component 120 with the right-most slot of its three orientation slots 200 (not shown) mated with the indexing boss 210 (not shown) of the baseplate component 110. This view also shows the void filler component 130 installed with alternate slots 250 mating with the external spline features 220 of the spacer component 120. In this assembly orientation, the horizontal axis 260 of the void filler component 130 makes a 3 degree counter-clockwise angle to the horizontal axis 270 of the baseplate component 110.

Figure 11:
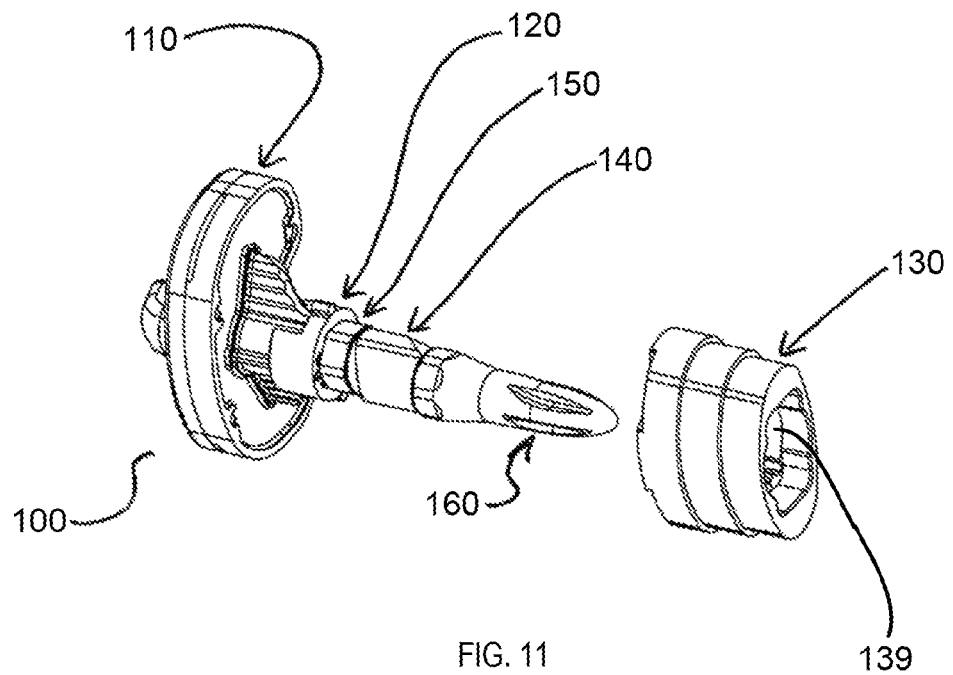
FIG. 11 is an isometric view of one embodiment of assembled baseplate, spacer, adapter and stem components showing a void filler component prior to being assembled to the assembled components.

FIG. 11 shows one embodiment of a final assembly of the joint prosthesis system 100, with void filler component 130 shown exploded. Once the spacer component 120 is in place on the baseplate component 110 it is held in place by preferably screwing down the adapter component 140 and tightening the locknut 150. Typically, the stem component 160 will also be installed at this time.

Void filler component 130 can be removed and/or installed while the baseplate component 110, the adapter component 140, the locknut 150 and the stem component 160 are attached to each other. This is a particular advantage if the joint prosthesis system 100 needs to be later removed from the patient, since the baseplate component 110 along with the adapter component 140, the locknut 150 and the stem component 160 can be removed from the patient as one assembly without needing to remove the void filler component 130 at the same time.

Figure 12:
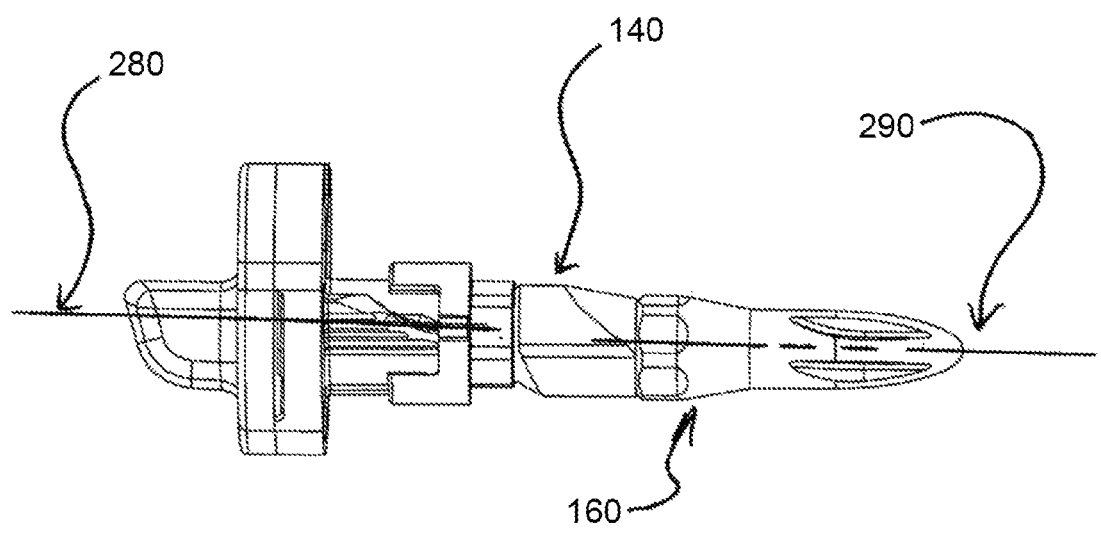
FIG. 12 is a side view of the assembled baseplate, spacer, adapter and stem components shown in FIG. 11.

One design detail shown in FIG. 12 is that the adapter component 140 is optionally offset such that a longitudinal axis 290 thereof is offset from a longitudinal axis 280 of baseplate component 110. This offset feature allows optimum coverage of the baseplate component 110 on the resected bone 180, and also ensures that the stem component 160 can be implanted down canal 190 of bone 180.

FIGS. 8, 9, and 10 show that this particular combination of components will provide relative rotation between the baseplate component 110 and void filler component 130 of 0°, +3°, and −3°. In instances where more rotation is necessary, the preferred method is to use a spacer component 120 for which the external spline features 220 are at a different angular orientation with respect to the orientation slots 200.

Figure 13:
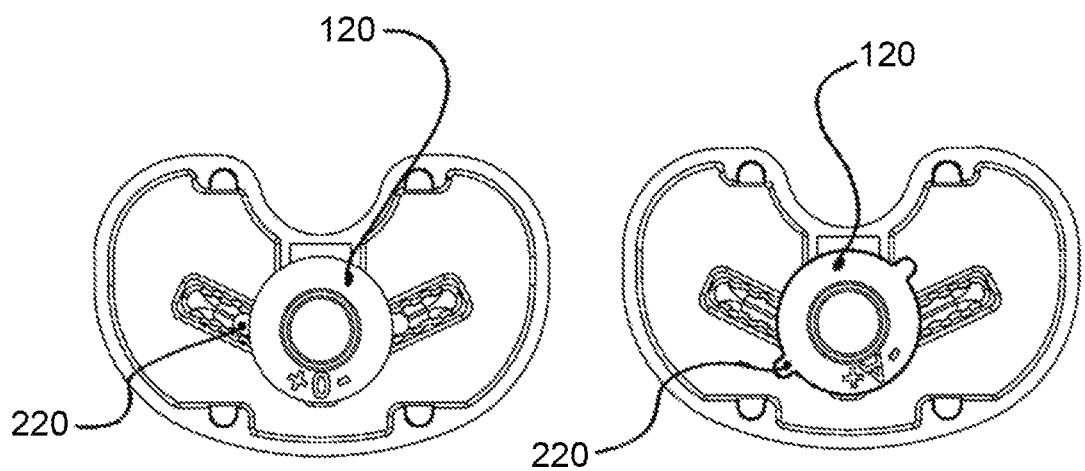
FIG. 13 shows on the left-hand side a bottom view of one embodiment of a spacer component assembled to a baseplate component and on the right-hand side a bottom view of the spacer component being angled with respect to the baseplate component.
Figure 14:
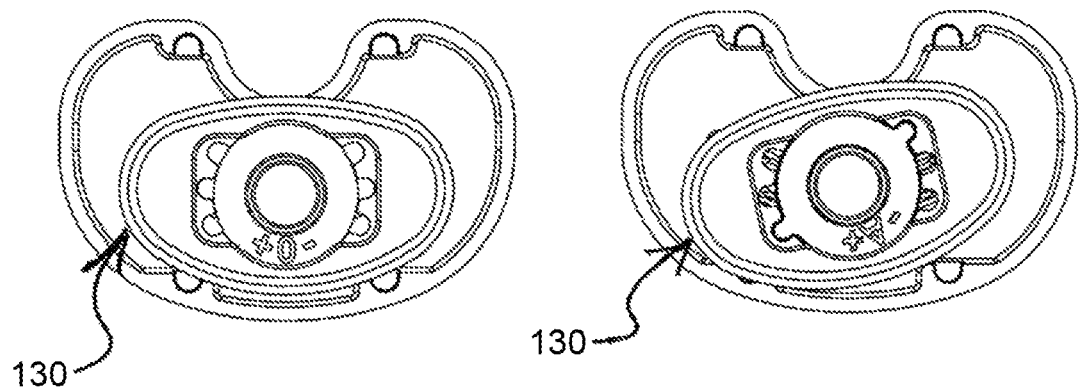
FIG. 14 shows on the left-hand side a bottom view of the assembled spacer and baseplate components shown on the left-hand side of FIG. 13 including a void filler component assembled to the assembled spacer and baseplate components and on the right-hand side is a bottom assembled view of the baseplate, spacer, and void filler components with the void filler component being angled with respect to the baseplate component.

FIGS. 13 and 14 show side-by-side views of (left) the previously shown −3°/0°/+3° spacer component 120, and (right) a spacer component 120 which will orient the void filler component 130 at −12°/−9°/−6°. Similarly, a spacer component 120 can have external spline features which will orient the void filler component 130 at +6°/+9°/+12°. While the external spline features may orient the void filler component at the above mentioned degrees, other embodiments may include a different number of splines and may orient the void filler component at different degrees.

Figure 15:
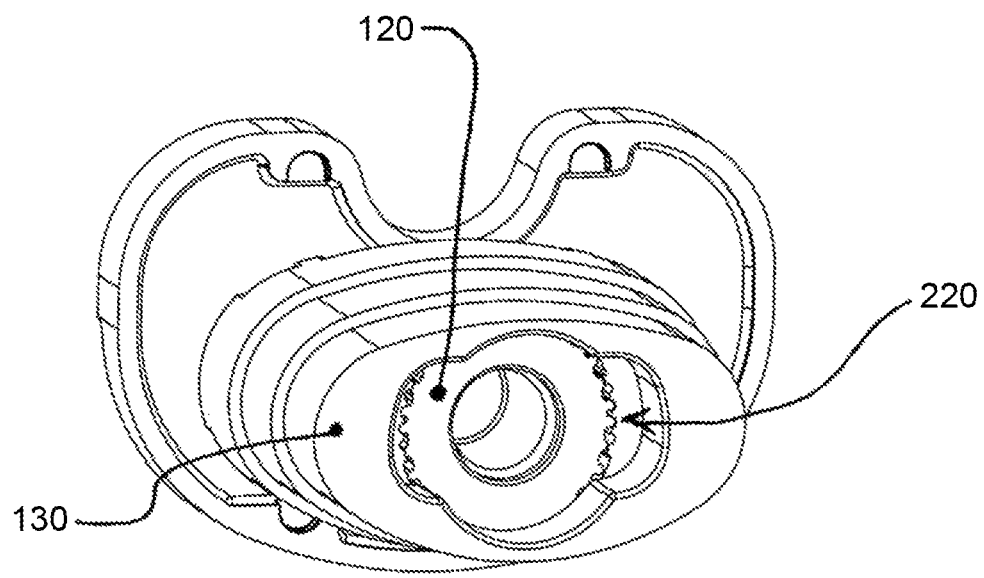
FIG. 15 shows an isometric view of one embodiment of assembled baseplate, spacer and void filler components with the spacer component having a plurality of protrusions engaged to a plurality of recesses of the void filler component.

In another embodiment, splines or protrusions (or other rotation prevention features) are located on one interface only. FIG. 15 shows an example of such a design in which finer splines 220 are used on only the interface between the spacer component 120 and the void filler component 130. As shown in FIG. 15, multiple splined features 220 are in contact with recesses on void filler component 130. This version of the design has the same angular adjustment capability as described with respect to the embodiment shown in FIGS. 2-14, with the multiple splined features 220 adding to the torsional strength of the assembled joint prosthesis.

Figure 16:
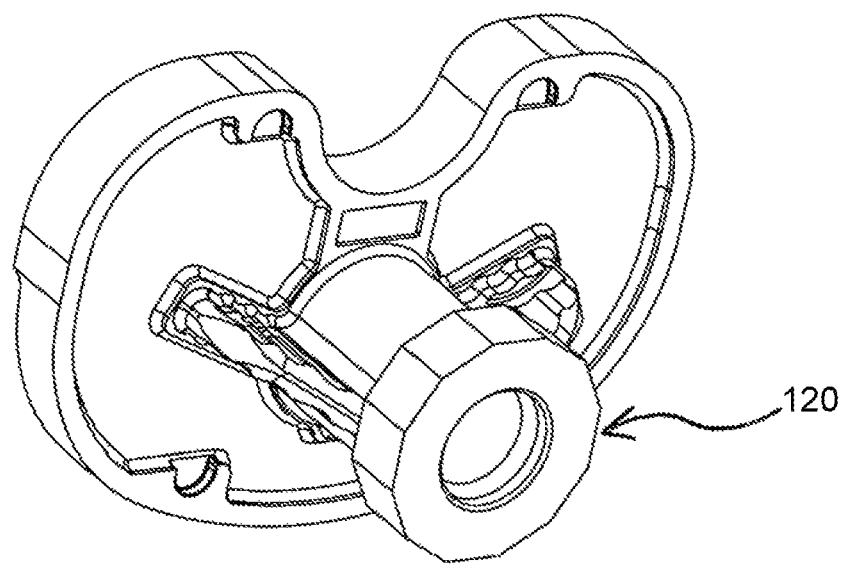
FIG. 16 shows an isometric view of one embodiment of a spacer component prior to being assembled to a baseplate component, the spacer component having an outer surface configured as a twelve-sided polygon.

In other embodiments, rotation control is provided by features other than splines. For example, semicircular protrusions on spacer component 120 may mate with semicircular clearances in the void filler component 130. As another example, the spacer component 120 can have an outer surface polygonal in shape, with a matching shape to an aperture in the void filler component. FIG. 16 shows a 12-sided polygon for this interface, which gives the same 30 degree angular rotation between locking positions that can be seen in the embodiment shown in FIG. 6. Many other shapes could be used to control rotation between the components of the prosthetic knee.

Other embodiments preferably include the use of different materials and/or coatings for each of the components of the system. In addition to the titanium alloy used in the preferred embodiment, cobalt chrome alloys, Nitinol, Stainless Steel, PEEK, and other metals, polymers or composites could be used in embodiments of this invention. Also, surface treatments to improve wear and/or galling resistance can be added. One example of this type of coating is titanium nitride. Other coatings preferably have the same beneficial effect. Surface treatments to encourage bony attachment such as porous coatings, hydroxyapatite, and TCP, for example, may be included in the design. Also, surface treatments or additives in one or more of the materials used for the components in the systems described herein could be used to provide beneficial effects such as anti-microbial, analgesic or anti-inflammatory properties.

Spacer component 120 and void filler component 130 are both preferably made of a titanium alloy. Other metals (such as a cobalt-chromium alloy), polymer, or composite materials could also be used.

The embodiments of the joint prosthesis system described herein are shown with respect to the tibial portion of a prosthetic knee. The present invention is equally applicable for use in both the femoral and tibial portions of a prosthetic knee, as well as in other joints such as the shoulder, hip, elbow, and wrist, for example.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A joint prosthesis system comprising:
a baseplate component having a top surface and a bottom surface, the bottom surface having a stem portion protruding outwardly therefrom;
a spacer component coupleable to the baseplate component, the spacer component having a top surface, a bottom surface, an inner surface, an outer surface, and an aperture extending through the top and bottom surfaces thereof, the outer surface having at least one protrusion extending outwardly therefrom; and
a void filler component coupleable to the spacer component, the void filler component having a top surface, a bottom surface, an inner surface, an outer surface, and an aperture extending through the top and bottom surfaces thereof, the inner surface having first and second recesses formed therein, the first and second recesses being located in an angular arrangement about a longitudinal axis of the joint prosthesis system,
wherein the void filler component is oriented in a first rotational position about the longitudinal axis of the joint prosthesis system when the aperture of the spacer component receives the stem portion of the baseplate component and the at least one protrusion of the spacer component is located in the first recess of the void filler component and in a second rotational position about the longitudinal axis of the joint prosthesis system when the aperture of the spacer component receives the stem portion of the baseplate component and the at least one protrusion of the spacer component is located in the second recess of the void filler component.

2. The joint prosthesis system of claim 1, wherein the stem portion has at least one rib located along at least a portion of a length thereof and the inner surface of the spacer component has at least one recess formed therein, and wherein the spacer component is coupled to the baseplate component when the aperture of the spacer component receives the stem portion of the baseplate component and the at least one rib of the stem portion is located in the at least one recess of the spacer component.

3. The joint prosthesis system of claim 1, further comprising first and second keels extending outwardly from the stem portion of the baseplate component.

4. The joint prosthesis system of claim 3, wherein the spacer component includes an aperture extending through the outer and inner surfaces thereof forming a first space and a second space located around a circumference of the spacer component such that a portion of the first keel can be received in the first space and a portion of the second keel can be received in the second space when the spacer component is coupled to the stem portion of the baseplate component.

5. The joint prosthesis system of claim 1, wherein the inner surface of the spacer component includes three recesses therein.

6. The joint prosthesis system of claim 5, wherein the three recesses are located approximately 30° apart from one another in the inner surface of the spacer component.

7. The joint prosthesis system of claim 1, wherein the inner surface of the void filler component includes three recesses therein.

8. The joint prosthesis system of claim 1, wherein the first and second recesses are separated at an angle less than 180° about the longitudinal axis.

9. The joint prosthesis system of claim 1, wherein the stem portion of the baseplate component has a longitudinal axis and the aperture of the spacer component has a longitudinal axis and when the spacer component is coupled to the stem portion of the baseplate component the longitudinal axes thereof are coaxial.

10. The joint prosthesis system of claim 1, wherein the stem portion of the baseplate component has a longitudinal axis and the aperture of the spacer component has a longitudinal axis and when the spacer component is coupled to the stem portion of the baseplate component the longitudinal axes thereof are parallel and offset from one another.

11. The joint prosthesis system of claim 9, wherein the aperture of the void filler component has a longitudinal axis and when the void filler component is coupled to the spacer component the longitudinal axes thereof are coaxial.

12. The joint prosthesis system of claim 9, wherein the aperture of the void filler component has a longitudinal axis and when the void filler component is coupled to the spacer component the longitudinal axes thereof are parallel and offset from one another.

13. The joint prosthesis system of claim 10, wherein the aperture of the void filler component has a longitudinal axis and when the void filler component is coupled to the spacer component the longitudinal axes thereof are coaxial.

14. The joint prosthesis system of claim 10, wherein the aperture of the void filler component has a longitudinal axis and when the void filler component is coupled to the spacer component the longitudinal axes thereof are parallel and offset from one another.

15. A joint prosthesis system comprising:
a baseplate component having a stem portion protruding outwardly from a bottom surface thereof, the stem portion having at least one rib extending outwardly therefrom;
a spacer component coupleable to the baseplate component, the spacer component having an aperture extending through top and bottom surfaces thereof and first and second recesses formed in an inner surface defined by the aperture, the first and second surfaces being located in an angular arrangement about a longitudinal axis of the joint prosthesis system; and
a void filler component coupleable to the spacer component, the void filler component having an aperture extending through top and bottom surfaces thereof;
wherein the spacer component is oriented in a first rotational position about the longitudinal axis of the joint prosthesis system when the at least one rib of the stem portion of the baseplate component is located in the first recess and in a second rotational position about the longitudinal axis of the joint prosthesis when the at least one rib of the stem portion of the baseplate component is located in the second recess of the spacer component.

16. The joint prosthesis system of claim 15, further comprising first and second keels extending outwardly from the stem portion of the baseplate component.

17. The joint prosthesis system of claim 16, wherein the spacer component includes an aperture extending through the outer surface and an inner surface thereof forming a first space and a second space located around a circumference of the spacer component such that a portion of the first keel can be received in the first space and a portion of the second keel can be received in the second space when the spacer component is coupled to the stem portion of the baseplate component.

18. The joint prosthesis system of claim 15, wherein the first and second recesses are separated at an angle being approximately 30°.

19. The joint prosthesis system of claim 18, wherein the inner surface of the void filler component includes a plurality of recesses located approximately 27° apart from one another.

20. A joint prosthesis system comprising:
a baseplate component having a stem portion, the stem portion having at least one rib extending therefrom;
a spacer component having a first end, a second end, an inner surface, and an outer surface, the outer surface having at least one protrusion extending therefrom, the inner surface being defined by an aperture extending through the first and second ends and having first and second spacer recesses formed therein, the first and second spacer recesses being located in an angular arrangement about a longitudinal axis of the prosthesis system such that the first and second spacer recesses are separated at a first angle; and
a void filler component having a first end, a second end, an inner surface, and an outer surface, the inner surface of the void filler component being defined by an aperture extending through the first and second ends of the void filler component and having a first and second filler recesses formed therein, the first and second filler recesses being located in an angular arrangement about a longitudinal axis of the prosthesis system such that the first and second filler recess are separated at a second angle.

21. The joint prosthesis system of claim 20, wherein the void filler component is coupled to the spacer component in a first angular orientation with respect to a horizontal axis of the baseplate component when the at least one rib is located within the first spacer recess and the at least one protrusion is located within the first filler recess, and in a second angular orientation with respect to the horizontal axis of the baseplate component when the at least one rib is located within the second spacer recess and the at least one protrusion is located within the second filler recess.

22. The joint prosthesis system of claim 21, wherein a third angle defined between the first angular orientation and the second angular orientation is substantially equal to a difference between the first and second angles.

23. The joint prosthesis system of claim 22, wherein the third angle is one of approximately three, six, nine or twelve degrees.

24. The joint prosthesis system of claim 21, wherein the first angle is approximately 30 degrees and the second angle is approximately 27 degrees.

* * * * *

UNITED STATES PATENT AND TRADEMARK OFFICE
CERTIFICATE OF CORRECTION

| | | |
|---|---|---|
| PATENT NO. | : 8,932,364 B2 | Page 1 of 1 |
| APPLICATION NO. | : 13/182841 | |
| DATED | : January 13, 2015 | |
| INVENTOR(S) | : Mark Mooradian, Jeffery Arnett and Joshua A. Butters | |

It is certified that error appears in the above-identified patent and that said Letters Patent is hereby corrected as shown below:

On the Title Page, Item (54) and in the Specification, column 1, replace "FILERS" with
-- FILLERS --.

In the Claims

In column 12, line 40, replace "having a first and second" with -- having first and second --.

Signed and Sealed this
Twenty-eighth Day of July, 2015

Michelle K. Lee
*Director of the United States Patent and Trademark Office*